United States Patent
Mathan et al.

(10) Patent No.: US 7,631,028 B2
(45) Date of Patent: Dec. 8, 2009

(54) STATISTICAL CONTROL OF ADAPTIVE OCULAR FILTER STABILITY

(75) Inventors: Santosh Mathan, Minneapolis, MN (US); Michael C. Dorneich, St. Paul, MN (US); Stephen D. Whitlow, St. Louis Park, MN (US)

(73) Assignee: Honeywell International Inc., Morristown, NJ (US)

( * ) Notice: Subject to any disclaimer, the term of this patent is extended or adjusted under 35 U.S.C. 154(b) by 887 days.

(21) Appl. No.: 11/224,332

(22) Filed: Sep. 12, 2005

(65) Prior Publication Data

US 2007/0239814 A1    Oct. 11, 2007

(51) Int. Cl.
*G06F 17/10*    (2006.01)
(52) U.S. Cl. .................................... 708/322
(58) Field of Classification Search .......... 708/322–323
See application file for complete search history.

(56) References Cited

U.S. PATENT DOCUMENTS

| | | | |
|---|---|---|---|
| 5,444,786 A * | 8/1995 | Raviv | 381/71.14 |
| 5,513,649 A | 5/1996 | Gevins et al. | |
| 5,602,927 A * | 2/1997 | Tamamura et al. | 381/71.4 |
| 6,732,129 B1 | 5/2004 | Ashjaee | |
| 2008/0013617 A1* | 1/2008 | Ooi | 375/232 |

OTHER PUBLICATIONS

He et al., "Removal of Ocular Artifacts from Electro-Encephalogram by Adaptive Filtering," Med. Biol. Eng. Comput., 2004, vol. 42, pp. 407-412, US.

* cited by examiner

*Primary Examiner*—Tan V Mai
(74) *Attorney, Agent, or Firm*—Fogg & Powers LLC

(57) ABSTRACT

An electroencephalograph system and method for controlling the stability of an adaptive filter during high noise spikes in ocular sensor channels. The method comprises receiving a signal from at least one sensor and determining when an adaptive filter algorithm is subject to becoming unstable based on a signal from the at least one sensor. Operation of the adaptive filter algorithm is suspended while the algorithm is subject to becoming unstable.

29 Claims, 4 Drawing Sheets

STATISTICAL CONTROL OF ADAPTIVE OCULAR FILTER STABILITY

GOVERNMENT LICENSE RIGHTS

The U.S. Government may have certain rights in the present invention as provided far by the terms of Government Contract # DAAD-16-03-C-0054 with the U.S. Army Natick/DARPA.

TECHNICAL FIELD

The present invention generally relates to electroencephalographs (EEG) and, in particular, to adaptive filter algorithms.

BACKGROUND

Electroencephalographs provide useful data on brain activity that is used for a variety of purposes, such as medical research and clinical treatment. EEG signals, however, often contain ocular artifacts produced by eye activity. These ocular artifacts adversely affect the data collected on brain activity. Consequently, adaptive filter algorithms, based on the Least Mean Square algorithm, have been developed to filter out ocular artifacts from EEG signals.

Adaptive filter algorithms use signals from ocular sensors, in conjunction with signals at EEG sites of interest, to derive an estimate of the noise from eye activity at various EEG sites. Once the adaptive filter algorithm has stabilized, these site specific noise estimates can be subtracted from the associated EEG site to produce cleaner EEG signals.

Current applications of adaptive filter algorithms are typically limited to controlled laboratory environments. In mobile, non-laboratory controlled environments, however, noise spikes in ocular sensor channels are often induced by non-ocular sources such as rubbing and sensor movement. These non-ocular sources can cause prolonged high amplitude spikes which in turn can prevent adaptive filter algorithms from converging within a reasonable period of time. When this occurs, the unstable filter algorithms corrupt the EEG signal and render the algorithms and EEG signals virtually useless.

For the reasons stated above, and for other reasons stated below which will become apparent to those skilled in the art upon reading and understanding the present specification, there is a need in the art for an electroencephalograph which is not susceptible to instability of an adaptive filter algorithm in the presence of prolonged high amplitude noise spikes in ocular sensor channels.

SUMMARY

Embodiments of the present invention solve problems with the susceptibility of an electroencephalograph to instability of an adaptive filter algorithm in the presence of prolonged high amplitude noise spikes in ocular sensor channels.

In one embodiment, a method for controlling stability of an adaptive filter is provided. The method comprises receiving a signal from at least one sensor, determining when an adaptive filter algorithm is subject to becoming unstable based on a signal from the at least one sensor, and suspending operation of the adaptive filter algorithm while the algorithm is subject to becoming unstable.

In another embodiment, a computer readable medium having computer-executable instructions for performing a method for controlling the stability of an adaptive filter is provided. The method comprises calculating a stability factor for data points contained in a signal from at least one sensor, comparing the calculated stability factor values to a stability factor threshold value, and suspending operation of an adaptive filter algorithm while the stability factor values exceed the stability factor threshold.

In another embodiment, an electroencephalograph (EEG) system is provided. The electroencephalograph system comprises at least one sensor, and a processing unit for receiving a signal from the at least one sensor, wherein, the processing unit determines when an adaptive filter algorithm is subject to becoming unstable and suspends operation of the adaptive filter algorithm during periods when the algorithm is subject to becoming unstable.

In yet another embodiment, an electroencephalograph processing unit is provided. The electroencephalograph processing unit comprises means for receiving a signal from at least one sensor, means for determining when an adaptive filter algorithm is subject to becoming unstable based on data received from the at least one sensor, and means for suspending operation of an adaptive filter algorithm for periods when it is determined that the adaptive filter algorithm is subject to becoming unstable.

The present invention together with the above and other advantages may best be understood from the following detailed description of the embodiments of the invention illustrated in the drawings, wherein:

DRAWINGS

DETAILED DESCRIPTION

Figure 1:
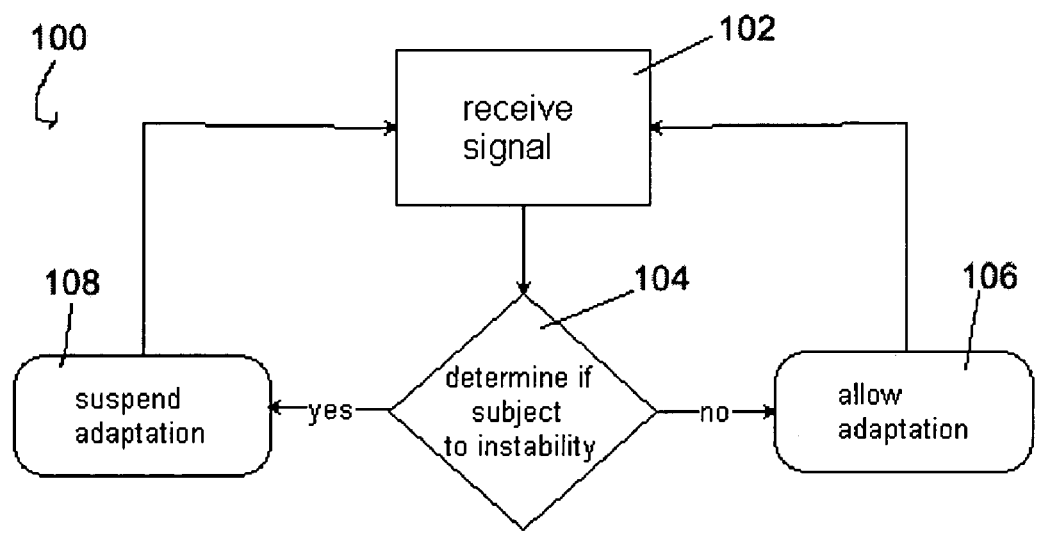
FIG. 1 is a flow chart showing a method of controlling the stability of an adaptive filter algorithm according to one embodiment of the present invention.

In the following detailed description, reference is made to the accompanying drawings that form a part hereof, and in which is shown by way of illustration specific illustrative embodiments in which the invention may be practiced. These embodiments are described in sufficient detail to enable those skilled in the art to practice the invention, and it is to be understood that other embodiments may be utilized and that logical, mechanical and electrical changes may be made without departing from the scope of the present invention. It should be understood that the exemplary method illustrated may include additional or fewer steps or may be performed in the context of a larger processing scheme. Furthermore, the method presented in the drawing figures or the specification is not to be construed as limiting the order in which the individual steps may be performed. The following detailed description is, therefore, not to be taken in a limiting sense.

Current applications of EEGs with adaptive filter algorithm are limited to controlled laboratory environments. In these controlled environments, adaptive filter algorithms function properly and provide a great benefit to EEGs by filtering out noise from eye movement. However, in mobile environments, the functionality of these same adaptive filter algorithms not only suffers but may become so impaired as to corrupt the entire EEG signal rendering the algorithms and data received essentially useless. If the benefits of adaptive filter algorithms are to be obtained in a mobile environment, the algorithms must be stabilized during high amplitude spikes. Embodiments of the present invention solve the problem of stabilization during high amplitude spikes enabling researchers to effectively take the unprecedented step of using electroencephalographs (EEG) with adaptive filter algorithms in mobile environments.

FIG. 1 is a flow chart showing a method 100 of controlling the stability of an adaptive filter according to one embodiment of the present invention. In some embodiments, instructions for carrying out the various methods, process tasks, calculations, and control functions are implemented in software programs, firmware or computer readable instructions. These instructions are typically stored on any appropriate medium used for storage of computer readable instructions such as floppy disks, conventional hard disks, CD-ROM, flash memory ROM, nonvolatile ROM, RAM, and other like medium. In other embodiments, the various methods, process tasks, calculations, and control functions are implemented through hardware circuits, such as op-amps, logic gates, etc.

At 102, a signal is received from at least one sensor. At 104, it is determined, based on the signal received, if the algorithm is subject to becoming unstable. If it is determined that the algorithm is not subject to becoming unstable, an adaptive filter algorithm is allowed to run at 106. If it is determined that the algorithm is subject to becoming unstable, the adaptive filter algorithm is suspended for that point. In some embodiments, the determination if the algorithm is subject to becoming unstable is made by calculating a stability factor. In one embodiment, the stability factor calculated is a z-score for data points in the signal.

Z-scores have two primary benefits. First, z-scores have the property of representing the likelihood of a given value occurring. For example, 68% of the points in a distribution lie below one standard deviation of the mean (z-score of 1), 95% of the points lie below two standard deviations of the mean (z-score of 2) and so on. Therefore, using the z-score as the stability factor provides an intuitive way of determining if a given value should be considered extreme such that the algorithm should be suspended. Second, z-scores standardize the values. Data values in a signal, such as voltage ranges, associated with EEG and ocular sensors vary from person to person and from moment to moment. Expressing these data values as z-scores provides a consistent and standardized way to express and evaluate the values regardless of the changes in person and time. An exemplary embodiment of a method using z-scores as a stability factor is discussed in more detail with regards to FIG. 2.

Figure 2:
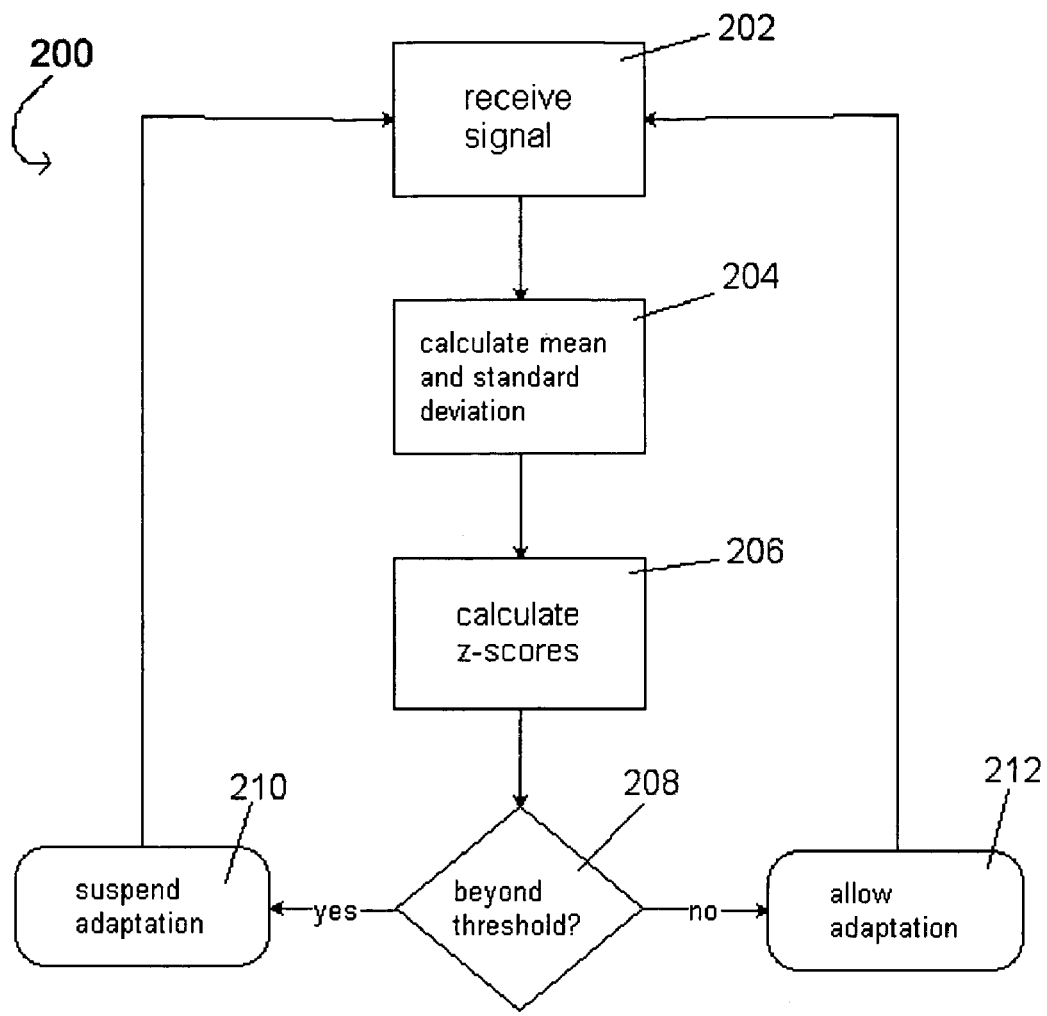
FIG. 2 is a flow chart showing a method of controlling the stability of an adaptive filter algorithm according to one embodiment of the present invention.

FIG. 2 is a flow chart showing a method of controlling the stability of an adaptive filter algorithm according to one embodiment of the present invention. At 202, a signal is received from at least one sensor. At 204, a mean and a standard deviation are calculated based on data points in the signal. In some embodiments, the mean and standard deviation are based on amplitudes in the signal. In one embodiment, the mean and standard deviation are continuously updated as more data points are received. In such embodiments, the mean and standard deviation are referred to as a running mean and a running standard deviation. In other embodiments, the mean and standard deviation are based on a baseline period where representative data points are collected. In other words, a sample is taken over a period of time when the sample does not have any extreme values. This sample is then used to calculate the mean and standard deviation rather than continuously updating the mean and standard deviation.

At 206, a z-score is calculated for each data point based on the mean and standard deviation calculated at 204. At 208, the z-score is compared to a threshold value for z-scores. If the z-score exceeds the threshold value, method 200 continues at 210 where an adaptive filter algorithm is suspended for that data point. Method 200 then repeats at 202 for a next data point in a signal received from an ocular sensor. If the z-score does not exceed the threshold value, method 200 continues at 212 where an adaptive filter algorithm is run to remove ocular artifacts from an EEG signal. Method 200 then repeats at 202 for a next data point in a signal received from the at least one sensor.

The method, therefore, suspends running an adaptive filter algorithm for as long as the z-score values exceed a z-score threshold, while allowing the algorithm to run as long as the z-score values do not exceed a z-score threshold. In some embodiments, a z-score threshold is pre-set and unchangeable. In other embodiments, a z-score threshold value adapts to environment conditions and the signal values received. In yet other embodiments, the z-score threshold value is adjustable by a user.

Figure 3:
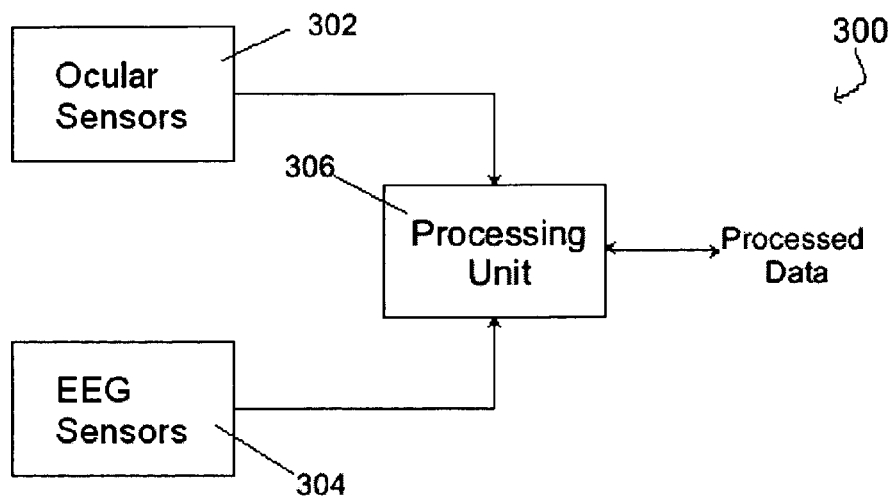
FIG. 3 is a block diagram of an electroencephalograph implementing one embodiment of the present invention for controlling the stability of an adaptive filter algorithm.

FIG. 3 is a block diagram of an electroencephalograph 300 implementing one embodiment of the present invention for controlling the stability of an adaptive filter algorithm. In one embodiment, a substantially continuous signal is received at processing unit 306 from one or more ocular sensors 302. Additionally, in one embodiment, a substantially continuous signal is received at processing unit 306 from one or more EEG sensors 304. In some embodiments, processing unit 306 is implemented through a processor and computer readable instructions, an exemplary embodiment of which is discussed in relation to FIG. 4. In such embodiments, instructions for carrying out the various methods, process tasks, calculations, control functions, and output of data are implemented in software programs, firmware or computer readable instructions. These instructions are typically stored on any appropriate medium used for storage of computer readable instructions such as floppy disks, conventional hard disks, CD-ROM, flash memory ROM, nonvolatile ROM, RAM, and other like medium. In other embodiments, processing unit 306 is implemented through an application specific integrated circuit (ASIC). In such embodiments, circuitry including but not limited to logic gates, counters, flip flops, resistors, capacitors, etc. are used. An exemplary embodiment of an implementation of processing unit 306 through an ASIC is discussed in more detail with regards to FIG. 5.

Processing unit 306 calculates a mean and standard deviation based on data points in the substantially continuous ocular signal. Additionally, processing unit 306 converts the data points to z-score values based on the mean and standard deviation. Processing unit 306 compares the calculated z-score values to a z-score threshold. If a z-score for a given data point from ocular sensors 302 is not within the threshold value, processing unit 306 suspends function of an adaptive filter algorithm for that data point. If a z-score for a given data point is within a z-score threshold, processing unit 306 allows an adaptive filter algorithm to run for that data point.

When allowed to run, an adaptive filter algorithm derives an estimate of noise from eye activity and subtracts that noise from an EEG signal producing a cleaner signal. In one embodiment, an adaptive filter algorithm forms a part of processing unit 306. In other embodiments, processing unit 306 outputs a signal to a separate processing unit, said signal indicates whether the separate processing unit should carry out instructions for an adaptive filter algorithm or suspend the algorithm temporarily. Finally, processing unit 306 outputs the processed data. In some embodiments, the processed data is output to a display unit. In other embodiments, the processed data is output to a printer. In yet other embodiments, the processed data is output to a storage device which stores the data for later use or display.

Figure 4:
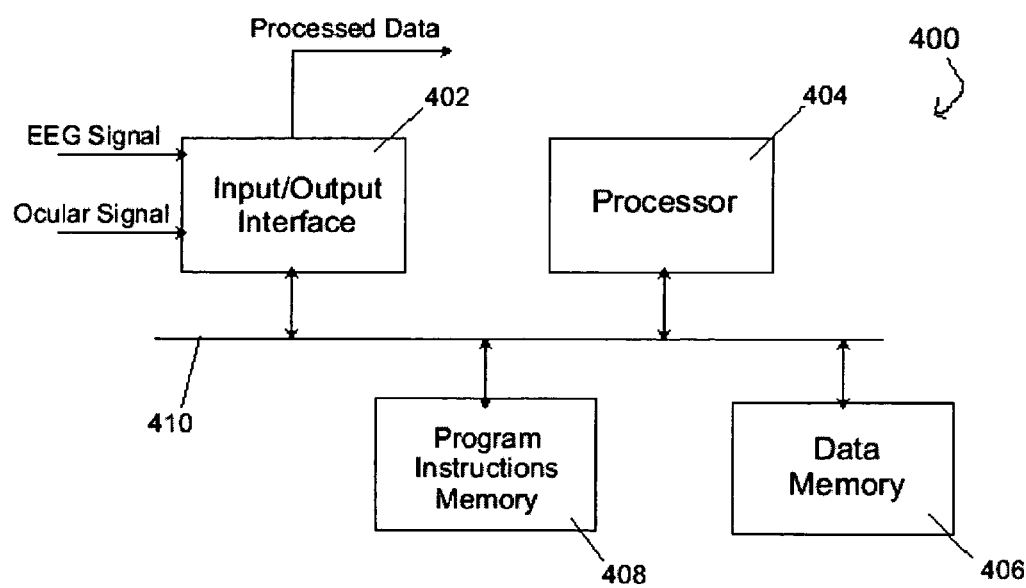
FIG. 4 is a block diagram of a processing unit of an electroencephalograph implementing one embodiment of the present invention for controlling the stability of an adaptive filter algorithm.

FIG. 4 is a block diagram of a processing unit of an electroencephalograph implementing one embodiment of the present invention for controlling the stability of an adaptive filter algorithm. Processing unit 400 consists of an input/output interface 402 which receives signals from external sensors and outputs processed data. The external sensors include, but are not limited to, ocular sensors and EEG sensors as shown in FIG. 3. Additionally, in some embodiments input/output interface 402 includes analog-to-digital/digital-to-analog converters (ADC/DAC). The ADC/DAC converts analog input to digital signals for processing by processing unit 400. In some embodiments, the ADC/DAC also converts the digitally processed data to analog signals for output to a display element or printer. Processing unit 400 also includes data bus 410 for transporting data to and from the various components of processing unit 400. In some embodiments, data received at input/output interface 402 is directly transferred to processor 404 for processing. In other embodiments, data received is first transferred to data memory 406 for storing the data until processed at a later time. In other embodiments, data received is transferred simultaneously to processor 404 and data memory 406. Data memory 406 includes, but is not limited to, any appropriate medium used for storage such as floppy disks, conventional hard disks, CD-ROM, flash memory ROM, nonvolatile ROM, RAM, and other like medium.

Processor 404 processes the data received according to program instructions stored in program instruction memory 408. Program instruction memory 408 includes, but is not limited to, any appropriate medium used for storage such as floppy disks, conventional hard disks, CD-ROM, flash memory ROM, nonvolatile ROM, RAM, and other like medium. In one embodiment, program instruction memory 408 and data memory 406 are physically the same memory storage device. In other embodiments, program instruction memory 408 and data memory 406 are physically distinct. Instructions stored in program instruction memory 408 direct processor 404 to process data according to a method for stabilizing an adaptive filter algorithm during high noise spikes as discussed above with respect to FIG. 1 and FIG. 2. Additionally, in some embodiments, program instruction memory 408 also contains instructions to direct processor 404 to run an adaptive filter algorithm on data received. Such instructions and methods are known to one of skill in the art. In other embodiments, the data output from input/output interface 402 is output to a separate processing unit for running an adaptive filter algorithm.

Figure 5:
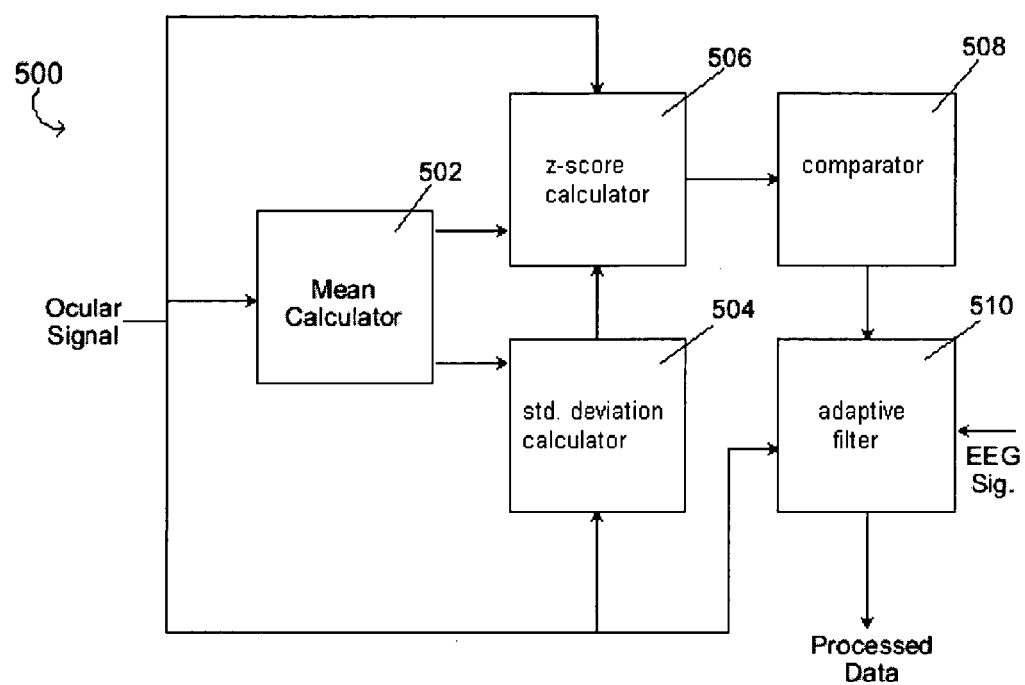
FIG. 5 is a block diagram of a processing unit of an electroencephalograph implementing one embodiment of the present invention for controlling the stability of an adaptive filter algorithm.

FIG. 5 is a block diagram of a processing unit of an electroencephalograph implementing one embodiment of the present invention for controlling the stability of an adaptive filter algorithm. Processing unit 500 is implemented as an ASIC using various circuits to perform necessary functions. The specific components to be used in each functional block to perform the necessary functions are known to one of skill in the art. For example, block 502 calculates a mean for the signal values. In one embodiment, to calculate a mean, block 502 uses a summation circuit. In one embodiment, this summation circuit is made from appropriate resistors and an OR logic gate. The skill of assembling and coupling appropriate components is known to one of skill in the art. Hence, the specific components are not discussed in detail in the present application. The blocks, therefore, represent the general functions needed to implement processing unit 500 in an ASIC.

An ocular signal is received at block 502 where a mean is calculated. The mean is output from block 502 to block 504. The ocular signal is also received at block 504. A standard deviation for values in the ocular signal is calculated at block 504 based on the ocular signal data values and the mean output from block 502. At block 506, the ocular signal and outputs from blocks 502 and 504 are received. At block 506, z-scores for values in the ocular signal are calculated based on the mean, standard deviation and ocular signal values. Block 506 then outputs z-scores to block 508. At block 508, the z-scores are compared to a z-score threshold. Based on the result of the comparison, block 508 outputs a signal to an adaptive filter at block 510.

If the z-scores exceed the z-score threshold, the signal indicates that the adaptive filter should be suspended. If the z-scores do not exceed the threshold, the signal indicates that the adaptive filter should be run. In some embodiments, block 510 is included as part of ASIC processing unit 500. In other embodiments, block 510 is separate from ASIC processing unit 500. At block 510, the ocular signal and an EEG signal are received in addition to the signal output from block 508. If the signal received from block 508 indicates that the z-score is within the threshold value, the adaptive filter algorithm at block 510 filters the EEG signal based on the ocular signal to produce a cleaner EEG signal which is output as processed data. If the signal received from block 508 indicates that the z-score exceeds the threshold value, the adaptive filter algorithm suspends operation until the signal indicates the z-score is within the threshold value.

Embodiments of the present invention provide a great improvement to EEGs. The embodiments enable EEGs to be used in mobile environments by suspending adaptive filter algorithms during the presence of high amplitude spikes. By doing so, the algorithms will not become unstable and can continue to be effective in producing cleaner EEG signals. In turn, EEGs can be more effectively used outside the controlled laboratory environment which gives researchers a new and improved opportunity for studying brain activity. It also enables for novel, practical applications based on EEG, including brain computer interfaces, adaptive assistance based on cognitive state estimation, to name a few.

Although specific embodiments have been illustrated and described herein, it will be appreciated by those of ordinary skill in the art that any arrangement, which is calculated to achieve the same purpose, may be substituted for the specific embodiment shown. This application is intended to cover any adaptations or variations of the present invention. Therefore, it is manifestly intended that this invention be limited only by the claims and the equivalents thereof.

What is claimed is:

1. A method for controlling stability of an adaptive filter, the method comprising:

receiving a signal from at least one ocular sensor and at least one electroencephalograph sensor;

determining when an adaptive filter algorithm is subject to becoming unstable based on the signal from the at least one ocular sensor, wherein the adaptive filter algorithm filters the signal from the at least one electroencephalograph sensor based, at least in part, on the signal from the at least one ocular sensor;

suspending operation of the adaptive filter algorithm while the adaptive filter algorithm is subject to becoming unstable; and outputting the filtered electroencephalograph signal when the adaptive filter algorithm is not subject to becoming unstable.

2. The method of claim 1, wherein determining when an adaptive filter algorithm is subject to becoming unstable includes:

calculating a stability factor for data points contained in the signal from the at least one ocular sensor; and comparing the calculated stability factor values to a stability factor threshold value.

3. The method of claim 2, wherein suspending operation of the adaptive filter further comprises:

suspending operating of the adaptive filter algorithm while the calculated stability factor exceeds the stability factor threshold.

4. The method of claim 3, wherein calculating a stability factor further comprises:

calculating a z-score value.

5. The method of claim 4, wherein calculating a z-score value includes:

calculating a mean based on data points in the signal from the at least one ocular sensor; and calculating a standard deviation for data points in the signal from the at least one ocular sensor based on the calculated mean and values of the data points.

6. The method of claim 5, wherein calculating a mean and standard deviation for data points includes:

calculating a running mean and a running standard deviation.

7. The method of claim 5, wherein calculating a mean and standard deviation for data points includes:

calculating a mean and standard deviation based on a baseline period where representative data points are collected.

8. A computer readable medium having computer-executable instructions for performing a method for controlling the stability of an adaptive filter, the method comprising:

calculating a stability factor for each of a plurality of data points contained in a signal from at least one sensor;

comparing the calculated stability factor values to a stability factor threshold value; and suspending operation of an adaptive filter algorithm while the stability factor values exceed the stability factor threshold.

9. The computer readable medium of claim 8 for performing a method, the method further comprising:

running the adaptive filter algorithm while calculated stability factor values do not exceed the stability factor threshold.

10. The computer readable medium of claim 8 for performing a method, wherein the at least one sensor includes:

at least one ocular sensor.

11. The computer readable medium of claim 8 for performing a method, wherein:

calculating the stability factor comprises calculating a z-score.

12. The computer readable medium of claim 11 for performing a method, wherein calculating a z-score includes:

calculating a mean based on data points in the signal from the at least one sensor; and calculating a standard deviation for data points in the signal from the at least one sensor based on the calculated mean and values of the data points.

13. The computer readable medium of claim 12 for performing a method, wherein calculating a mean and standard deviation for data points includes:

calculating a running mean and running standard deviation.

14. The computer readable medium of claim 12 for performing a method, wherein calculating a mean and standard deviation based on data points includes:

calculating a mean and standard deviation based on a baseline period where representative data points are collected.

15. An electroencephalograph (LEG) system, the system comprising:

at least one sensor; and a processing unit for receiving a signal from the at least one sensor, wherein, the processing unit determines when an adaptive filter algorithm is subject to becoming unstable and suspends operation of the adaptive filter algorithm during periods when the algorithm is subject to becoming unstable.

16. The electroencephalograph system of claim 15, wherein the at least one sensor includes:

at least one ocular sensor; and at least one electroencephalograph sensor.

17. The electroencephalograph system of claim 15, wherein the processing unit further comprises:

an input/output interface for receiving a signal from the at least one sensor and for outputting processed data;

a processor for processing data to be output by the input/output interface;

a program instructions memory for storing instructions which direct the processor to determine when the adaptive filter algorithm is subject to becoming unstable by calculating a stability factor and comparing that factor to a stability factor threshold, wherein the adaptive filter algorithm is subject to becoming unstable when the calculated stability factor exceeds the stability factor threshold;

a data memory for storing data received from the at least one sensor for use by the processor; and a bus for coupling and transferring data between the input/output interface, processor, program instructions memory, and data memory.

18. The electroencephalograph system of claim 17, wherein instructions for calculating a stability factor stored in the program instruction memory include:

instructions for calculating a z-score.

19. The electroencephalograph system of claim 18, wherein instructions for calculating a z-score include:

instructions for calculating a mean based on data points in a signal from the at least one sensor; and instructions for calculating a standard deviation for data points in a signal from the at least one sensor based on the calculated mean and values of the data points.

20. The electroencephalograph system of claim 15, wherein the processing unit includes:

at least one circuit which determines when the adaptive filter algorithm is subject to becoming unstable by calculating a stability factor and comparing the calculated stability factor to a stability factor threshold, wherein the adaptive filter algorithm is subject to becoming unstable when the calculated stability factor exceeds the stability factor threshold.

21. The electroencephalograph system of claim 20, wherein the at least one circuit further comprises:
- a first circuit for calculating a mean based on data points in the signal from the at least one sensor;
- a second circuit for receiving an output from the first circuit and for receiving the signal from the at least one sensor, wherein the second circuit calculates a standard deviation for data points in the signal from the at least one sensor based on the output received from the first circuit and the values of the data points in the signal from the at least one sensor;
- a third circuit for receiving an output from the first and second circuits and for receiving the signal from the at least one sensor, wherein the third circuit calculates a z-score based on the output received from the first and second circuits and the values of the data points in the signal from the at least one sensor, the z-score being the stability factor; and
- a fourth circuit for receiving a z-score output from the third circuit, for comparing the output of the third circuit to a z-score threshold, and for outputting a signal to suspend operation of an adaptive filter algorithm if the z-score output from the third circuit exceeds the z-score threshold.

22. The electroencephalograph system of claim 21, wherein;
- the first circuit calculates a running mean; and
- the second circuit calculates a running standard deviation.

23. The electroencephalograph system of claim 21, wherein;
- the first circuit calculates the mean based on a baseline period where representative data points are collected; and
- the second circuit calculates the standard deviation based on the baseline period where representative data points are collected.

24. An electroencephalograph processing unit, comprising:
- means for receiving a signal from at least one sensor;
- means for determining when an adaptive filter algorithm is subject to becoming unstable based on data received from the at least one sensor; and
- means for suspending operation of the adaptive filter algorithm for periods when it is determined that the adaptive filter algorithm is subject to becoming unstable.

25. The electroencephalograph processing unit of claim 24, wherein the means for receiving the signal from the at least one sensor comprises;
- an input interface for receiving the signal from the at least one sensor.

26. The electroencephalograph processing unit of claim 24, wherein the means for determining when the adaptive filter is subject to becoming unstable includes:
- means for calculating a stability factor for the adaptive filter algorithm based on data from the at least one sensor; and
- means for comparing the calculated stability factor to a stability factor threshold, wherein the adaptive filter algorithm is subject to becoming unstable when the calculated stability factor exceeds the stability factor threshold.

27. The electroencephalograph processing unit of claim 26, wherein the means for calculating the stability factor includes:
- a processor for processing data received from the at least one sensor; and
- a memory for storing instructions used by the processor to calculate the stability factor based on data received from the at least one sensor.

28. The electroencephalograph processing unit of claim 26, wherein the means for comparing the calculated stability factor to the stability factor threshold includes:
- at least one circuit which receives an input containing the stability factor and compares the input to the stability factor threshold.

29. The electroencephalograph processing unit of claim 26, wherein:
- the stability factor is a z-score

* * * * *

UNITED STATES PATENT AND TRADEMARK OFFICE
CERTIFICATE OF CORRECTION

| | | |
|---|---|---|
| PATENT NO. | : 7,631,028 B2 | Page 1 of 1 |
| APPLICATION NO. | : 11/224332 | |
| DATED | : December 8, 2009 | |
| INVENTOR(S) | : Mathan et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1122 days.

Signed and Sealed this

Second Day of November, 2010

David J. Kappos
*Director of the United States Patent and Trademark Office*